United States Patent [19]

Trenkle et al.

[11] 4,209,542
[45] Jun. 24, 1980

[54] PROCESS FOR AUGMENTING OR ENHANCING THE AROMA OR TASTE OF A FOODSTUFF BY ADDING TO A FOODSTUFF A MIXTURE OF 1-ACYL-2,6,6-TRIMETHYLCYCLOHEXENE DERIVATIVES

[75] Inventors: Robert W. Trenkle, Bricktown; Braja D. Mookherjee, Holmdel; Robin Kasper, Eatontown; Manfred H. Vock, Locust; Joaquin Vinals, Red Bank, all of N.J.; Jacob Kiwala, Brooklyn, N.Y.; Frederick L. Schmitt, Holmdel, N.J.

[73] Assignee: International Flavors & Fragances Inc., New York, N.Y.

[21] Appl. No.: 39,360

[22] Filed: May 15, 1979

Related U.S. Application Data

[62] Division of Ser. No. 965,418, Dec. 1, 1978, Pat. No. 4,172,850.

[51] Int. Cl.² .................... A23L 1/226; A23L 1/235
[52] U.S. Cl. .................................................. 426/538
[58] Field of Search .......................................... 426/538

[56] References Cited

FOREIGN PATENT DOCUMENTS 2244680 8/1973 Fed. Rep. of Germany .

OTHER PUBLICATIONS

Schulte-Elte, et al., CA:79:42041a (p. 321), 1973.

*Primary Examiner*—Joseph M. Golian
*Attorney, Agent, or Firm*—Arthur L. Liberman; Franklin D. Wolffe

[57] ABSTRACT

Described is a process for augmenting or enhancing the aroma or taste of a foodstuff by adding to said foodstuff a mixture of compounds having the structures:

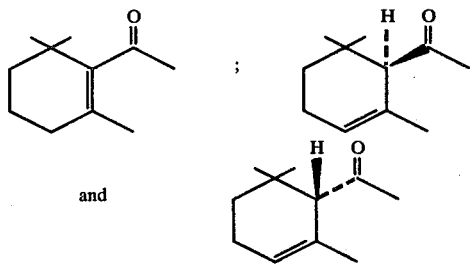

and wherein said mixture contains 30% of the compounds having the structures:

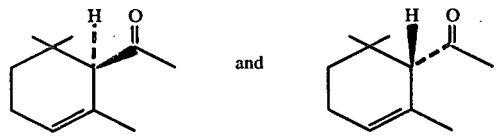

and and 60% of the compound having the structure:

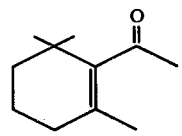

2 Claims, 5 Drawing Figures

GLC PROFILE FOR EXAMPLE I

NMR SPECTRUM FOR EXAMPLE I, PEAK 2.

NMR SPECTRUM FOR EXAMPLE I, PEAK 3.

IR SPECTRUM FOR EXAMPLE I, PEAK 2.

IR SPECTRUM FOR EXAMPLE I, PEAK 3.

PROCESS FOR AUGMENTING OR ENHANCING THE AROMA OR TASTE OF A FOODSTUFF BY ADDING TO A FOODSTUFF A MIXTURE OF 1-ACYL-2,6,6-TRIMETHYLCYCLOHEXENE DERIVATIVES

This application is a divisional of application for U.S. Pat. Ser. No. 965,418, filed on Dec. 1, 1978, now U.S. Pat. No. 4,172,850, issued on Oct. 30, 1979.

BACKGROUND OF THE INVENTION

The present invention provides the compounds having the generic structure:

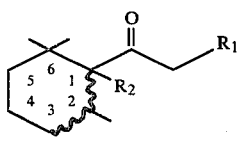

wherein $R_1$ is hydrogen or ethylidene having the structure:

and $R_2$ is hydrogen or no group; wherein one of the wavy lines is a carbon-carbon double bond and the other of the wavy lines is a carbon-carbon single bond; with the proviso that when the $\Delta^{2,3}$ bond is a carbon-carbon double bond, $R_2$ is hydrogen and $R_2$ and the moiety:

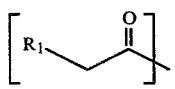

are so juxtaposed that the molecule having the structure:

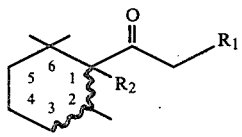

exists in two different isomeric forms; a "+" and a "−" form. Such compounds are provided by a novel process of our invention described hereinafter which gives rise to novel intermediates including the compounds having the generic structure:

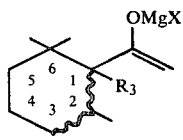

wherein X is chloro, bromo or iodo, $R_3$ is hydrogen or no group; wherein one of the wavy lines is a carbon-carbon double bond and the other of the wavy lines is a carbon-carbon single bond; with the proviso that when the $\Delta^{2,3}$ bond is a carbon-carbon double bond, then $R_3$ is hydrogen and $R_3$ and the moiety:

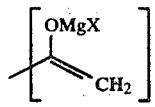

are so juxtaposed that the molecule having the structure:

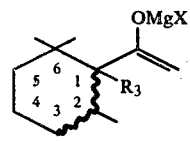

exists in two different forms; a "+" and a "−" form.

Compounds produced using the processes of our invention including a number of the intermediates produced are useful for their organoleptic properties in perfumes, perfumed articles, foodstuffs, foodstuff flavoring compositions, chewing gums, toothpastes, medicinal products, tobaccos, tobacco flavoring compositions, substitute tobaccos and substitute tobacco flavoring compositions.

In the perfumery art, there is a considerable need for substituents having sweet, floral, fruity, rose-like, minty/camphoraceous aromas with floral, hay-like, musty backgrounds and tobacco nuances. Specifically described herein are materials having such organoleptic profiles but which do not discolor with age. Such fragrance materials have a wide utilization in the presence of these perfume compounds. A limited amount of such materials that give rise to these properties is available from natural sources but the natural materials are subject to wide variations in quality, or are expensive, and/or often in critically short supply. This particularly holds true for the use of alpha damascone, beta damascone and mixtures of alpha damascone and beta damascone.

In addition, there is a continuing search for food flavor compositions which can vary, fortify, modify, enhance, augment or otherwise improve the flavor and/or aroma of foodstuffs, medicinal products, toothpastes, and chewing gums. To be satisfactory, such compositions should be stable, non-toxic and blendable with other ingredients to provide their own unique flavor and aroma nuances without detracting from the co-ingredients of the formulations in which they are used. Preferably, such compositions should be naturaly occurring or present in natural foodstuffs so that their ingestible safety can be readily recognized. These materials should be capable of being synthesized in a simple and economical manner. The need for safe flavors in the mint, lemon and tropical fruit flavor area is well known particularly in the ice cream and yogurt flavor areas. More specifically, there is a need for the development of non-toxic materials which can replace natural materials not readily available, having herbaceous, earthy, patchouli-like, damascenone-like, lemony and minty aroma and flavor characteristics.

In tobacco flavoring art (pertaining to tobaccos and substitute tobaccos) there is a considerable need for substituents having musty-floral, slightly sweet, fruity and damascenone-like aromas and tastes in tobacco prior to smoking and sweet, Virginia tobacco-like notes on smoking in both the main stream and the side stream.

Specifically described herein are materials having such an organoleptic profile but which do not discolor with age.

The instant invention provides the foregoing, which the prior art has heretofore fails to provide. Furthermore, nothing in the prior art shows the unexpected, unobvious and advantageous value of the compounds having the structures:

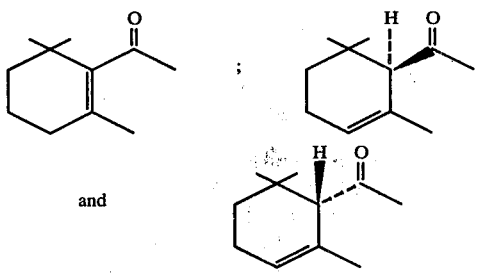

and for their organoleptic properties.

The compounds having the structures:

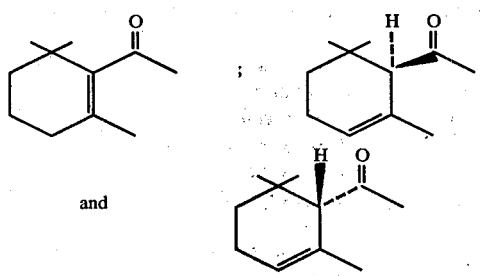

and are disclosed in the prior art at:
  Chem. Abstracts, Vol. 78, No. 110669t (Abstracts of J. Org. Chem. 1973, 38 [5], 894-6);
  Chem. Abstracts, Vol. 80, No. 27395w (Abstracts of J. Chem. Soc., Chem. Communications 1973 [19], 7842; and at
  Chem. Abstracts, Vol. 79, No. 42041a (Abstract of German Offlegungschrift 2,244,680). German Offlegungschrift 2,244,680 includes a genus which could read on the compound having the structure:

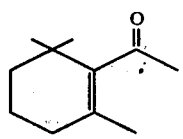

but no specific disclosure thereof is made in said German Offlegungschrift.

In addition, the preparations of these compounds have been carried out in a rather complex manner as is shown in:
  Chem. Abstracts 54:345f (U.S. Pat. No. 2,853,520);
  Chem. Abstracts, Vol. 50, 8540h (Abstract of Chanley, et al, J. Am. Chem. Soc. 77, 6056-7 [1955]);
  Chem. Abstracts 50:15442b (Abstract of Landor, J. Chem. Soc., 1956, 1015-1019);
  Chem. Abstracts, Vol. 48, 13644i (Abstract of Newman, J. Am. Chem. Soc., 75, 4740-2 [1953]); and
  Chem. Abstracts, Vol. 47:1098h (Abstract of Henbest, et al, J. Am. Chem. Soc., 1952, 1150-4)

Nothing in the prior art, however, discloses a process whereby a compound having the structure:

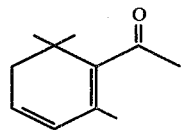

can be hydrogenated using a Lindlar catalyst to form compounds having the structures:

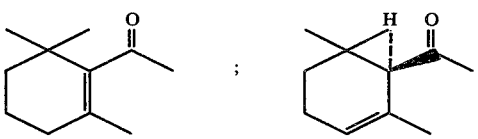

and

Another group of products produced as a result of using the processes of our invention are alpha-damascone and beta-damascones having the structures:

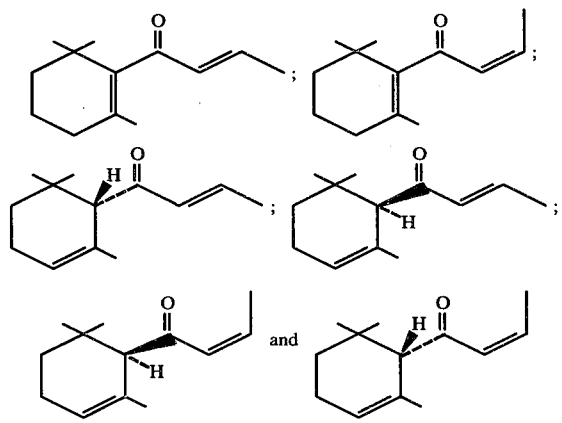

and

These compounds are shown to be useful for their organoleptic properties by Kovats at Chem. Abstracts, Vol. 74, page 76564k ("Cycloaliphatic Unsaturated Ketones for Use as Perfumes").

Mixtures, presumably predominantly cis,trans-Δ-damascone with minor amounts of trans, trans-Δ-damascone have been produced by Ayyar, Cookson and Kagi as set forth in J. Chem. Soc., Perkin Trans. 1, 1975 (17) 1727-36 [Title: "Synthesis of α-Damascone[-trans-1-(2,6,6-Trimethylcyclohex-3-enyl)but-2-en-1-one] and β-Damascenone [trans-1-(2,6,6-Trimethylcyclohexa-1,3-dienyl)but-2-en-1-one]"]. The reaction sequence of the Ayyar synthesis of compositions presumed to be predominantly cis, trans-Δ-damascone with minor amounts of trans, trans-Δ-damascone is as follows:

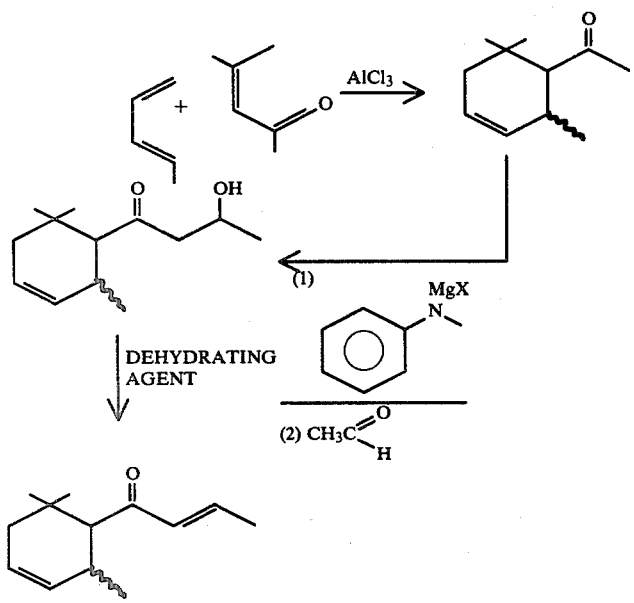

wherein the wavy line is representative of a "cis" or "trans" configuration of the methyl moiety with respect to the acetyl or crotonoyl moiety, both of which are bonded to the cyclohexenyl moiety, the "cis" isomer presumably being the major isomer and the "trans" isomer presumably being the minor isomer in this reaction sequence.

Nothing in the prior art, however, teaches the usefullness of the processes of our invention or the usefullness of the compounds having the structures:

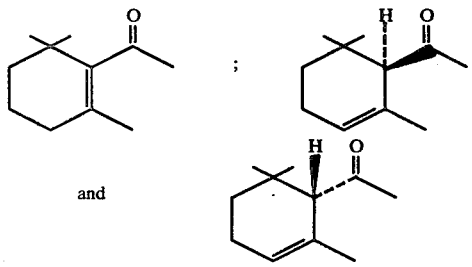

for their organoleptic properties.

Figure 3:
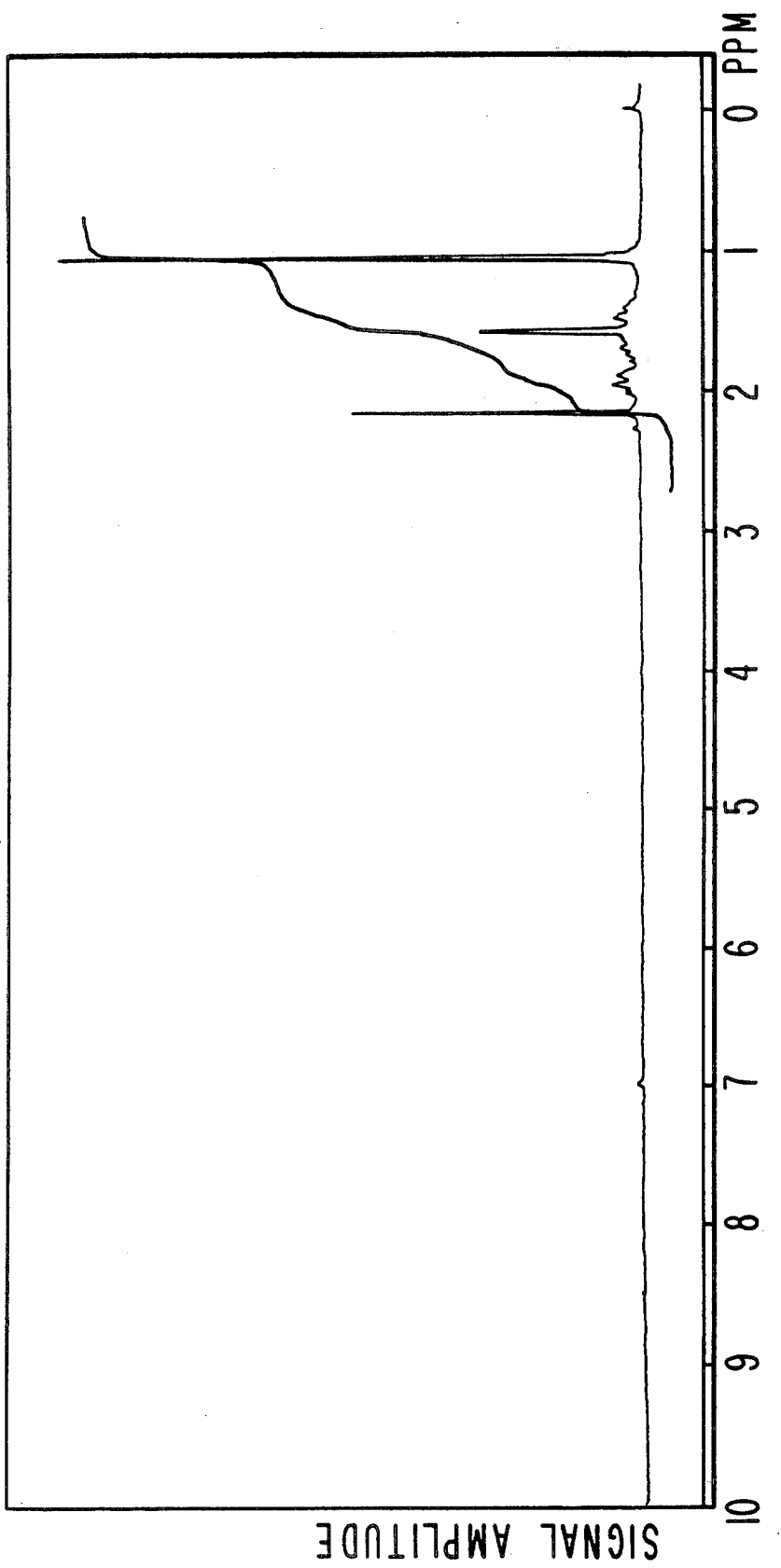

FIG. 3 is the NMR spectrum of the compound of peak 3 of Example I, having the structure:

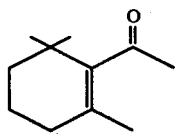

Figure 4:
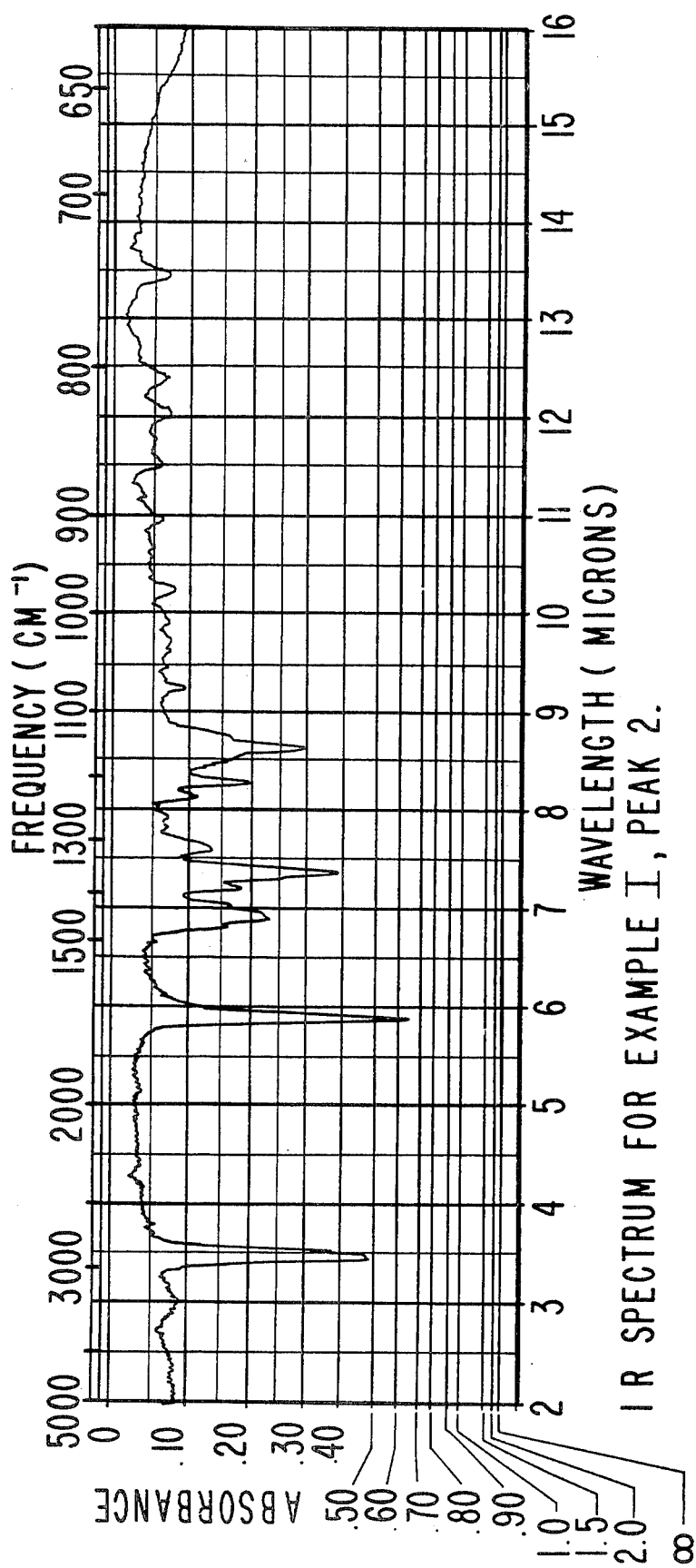

FIG. 4 is the infrared spectrum for the compounds of peak 2 of Example I containing compounds having the structures:

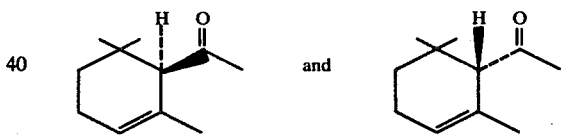

Figure 5:
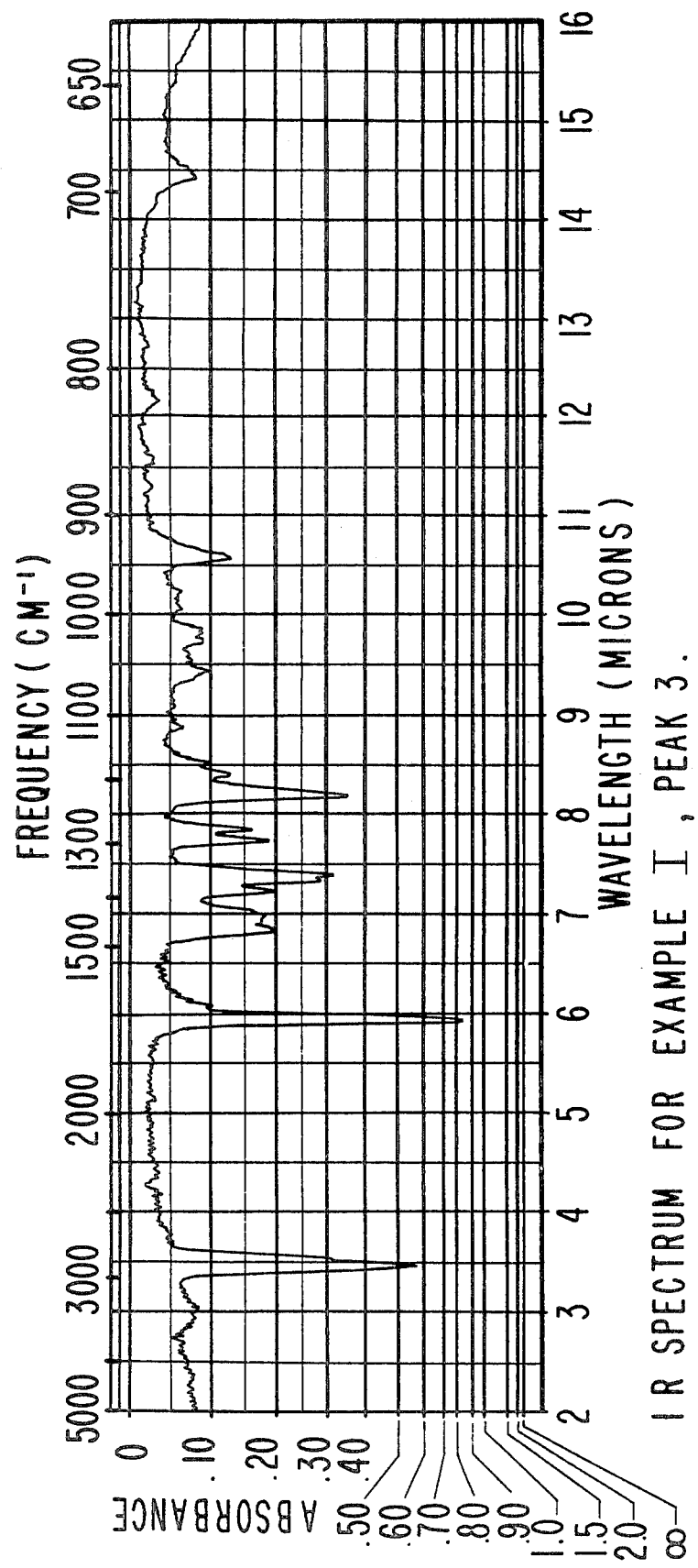

FIG. 5 is the infrared spectrum for peak 3 of Example I having the compound having the structure:

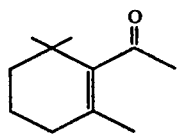

THE INVENTION

The present invention provides compounds having the generic structure:

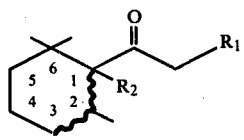

wherein $R_1$ is hydrogen or ethylidene having the structure:

$R_2$ is hydrogen or no group; one of the wavy lines is a carbon-carbon double bond and the other of the wavy lines is a carbon-carbon single bond; with the proviso that when the $\Delta^{2,3}$ bond is a carbon-carbon double bond then $R_2$ is hydrogen and $R_2$ and the moiety:

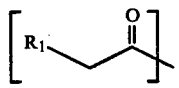

are so juxtaposed that the molecule:

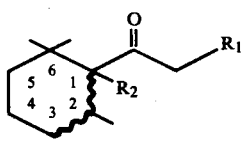

exists in two different isomeric forms; a "+" and a "−" form. The present invention also provides intermediates having the generic structure:

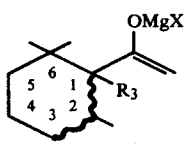

wherein X is chloro, bromo or iodo and $R_3$ is hydrogen or no group; and one of the wavy lines is a carbon-carbon double bond and the other of the wavy lines is a carbon-carbon single bond; with the proviso that when the $\Delta^{2,3}$ is a carbon-carbon double bond that $R_3$ is hydrogen and $R_3$ and the moiety:

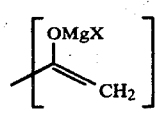

are so juxtaposed that the molecule having the structure:

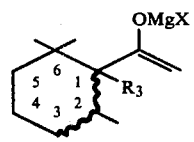

exists in two different isomeric forms; a "+" form and a "−" form. The present invention also provides processes for preparing such compounds and intermediates using the compound having the structure:

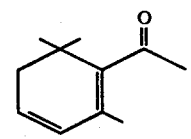

as a precursor. Such a process is summarized and illustrated by the reaction sequence:

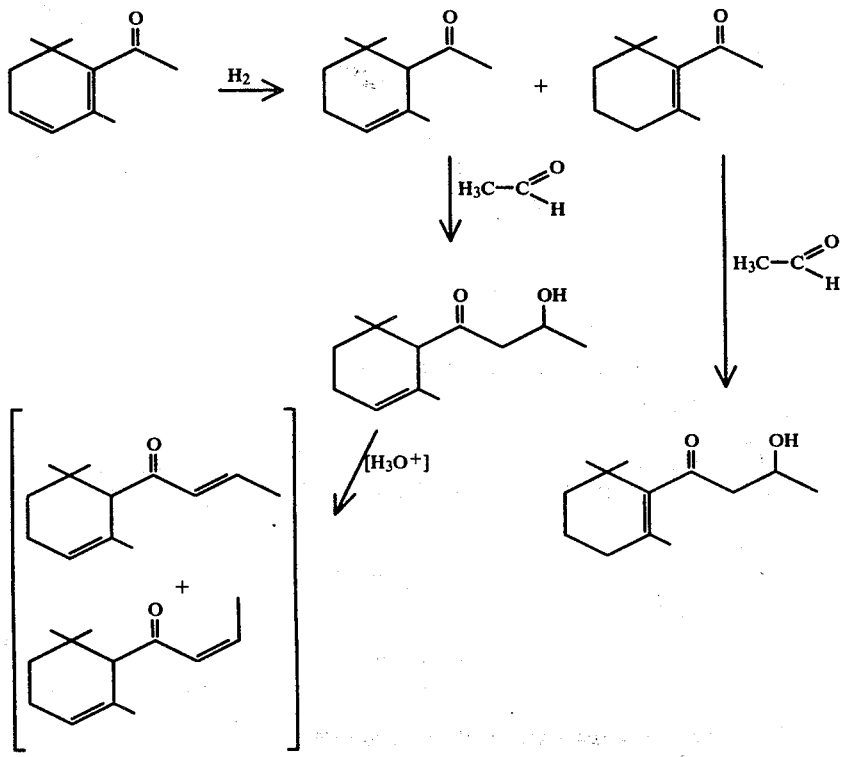

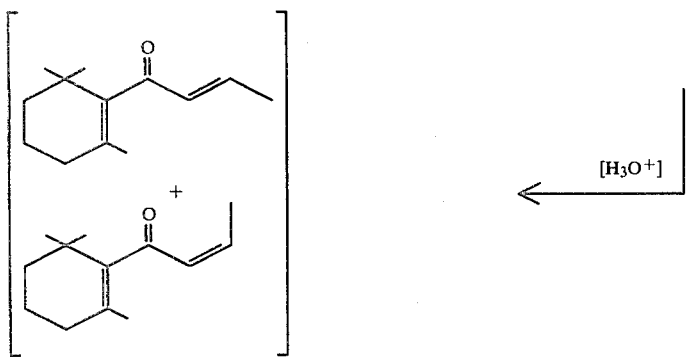

The 1-acyl-2,6,6-trimethylcyclohexene derivatives of our invention produced according to the process of our invention are capable of augmenting or enhancing mint, lemon and tropical fruit flavors by imparting thereto herbaceous, earthy, patchouli-like, damascenone-like, lemony and minty aroma and flavor characteristics.

The 1-acyl-2,6,6-trimethylcyclohexene derivatives of our invention as well as mixtures thereof are also capable of modifying or enhancing the odor characteristics of perfume compositions, colognes and perfumed articles (including soaps, nonionic, anionic and cationic detergents and fabric softener articles) by imparting thereto sweet, floral, fruity, rose-like and minty/camphoraceous aromas with floral, hay-like and musty background notes and tobacco nuances, thus fulfilling a need in the field of perfumery.

In tobacco, tobacco flavoring compositions, substitute tobacco and substitute tobacco flavoring compositions, the 1-acyl-2,6,6-trimethylcyclohexene derivatives of our invention produced according to the process of our invention impart musty-floral, slightly sweet, fruity and damascenone-like aroma notes to tobacco and substitute tobaccos prior to smoking and sweet, Virginia-like tobacco notes to tobacco on smoking in the main stream and in the side stream.

The 1-acyl-2,6,6-trimethylcyclohexene derivatives of our invention are produced by first reacting 2,6,6-trimethyl-1-acetyl-cyclohexene-1 having the structure:

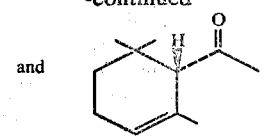

with hydrogen over a catalyst such as a Lindlar catalyst (palladium suspended on calcium carbonate) thus forming a mixture of 1-acetyl-2,6,6-trimethylcyclohexene-1 and cyclohexene-2 compounds. This resulting mixture of compounds having the structures:

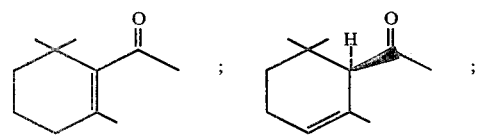

and 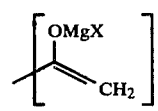

may either be separated whereupon the resulting substantially pure organic compounds can be used "as is" for their organoleptic properties or the resulting substantially pure organic compounds can be further reacted. On the other hand, the resulting mixture can be used as is as an intermediate or for its organoleptic properties. In any event, the 1-acetyl-2,6,6-trimethylcyclohexene-1 and/or 2 derivatives thus produced may be individually or in admixture further reacted with a lower alkyl magnesium halide (lower alkyl Grignard reagent) in order to produce an organometallic salt having the structure:

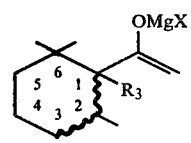

wherein X is chloro, bromo or iodo; $R_3$ is hydrogen or no group; wherein one of the wavy lines is a carbon-carbon double bond and the other of the wavy lines is a carbon-carbon single bond; with the proviso that when the $\Delta^{2,3}$ bond is a carbon-carbon double bond, then $R_3$ is hydrogen and $R_3$ and the moiety:

$$\begin{bmatrix} OMgX \\ | \\ \diagup\hspace{-0.3em}\diagdown CH_2 \end{bmatrix}$$

are so juxtaposed that the molecule:

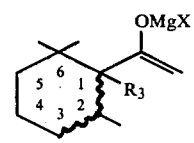

exists in two different forms, a "+" and a "−" form. The resulting organometallic compound(s) is (are) then reacted with acetaldehyde followed by hydrolysis in order to produce compounds either in pure form or in admixture (depending on whether the starting materials are in "pure form" or in "admixture") having one or more of the structures:

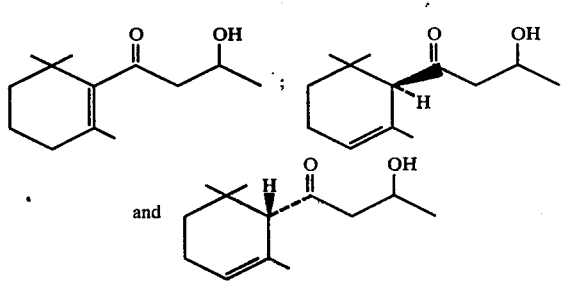

The resulting hydroxy ketone derivatives can be separated (as by distillation) and used for their organoleptic properties individually or they can be separated and further reacted (e.g., dehydrated) or they can be utilized "as is" in admixture for their organoleptic properties. When the resulting hydroxy ketones having the structures:

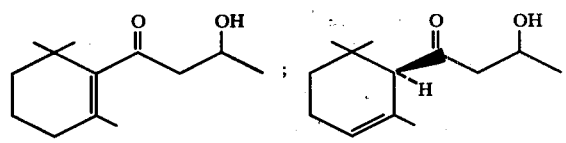

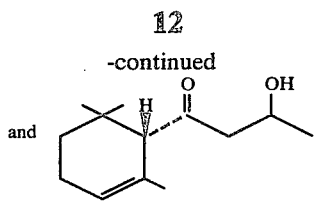

are either separately or in admixture dehydrated, each of the compounds or the compounds in admixture gives rise to compounds having the structures:

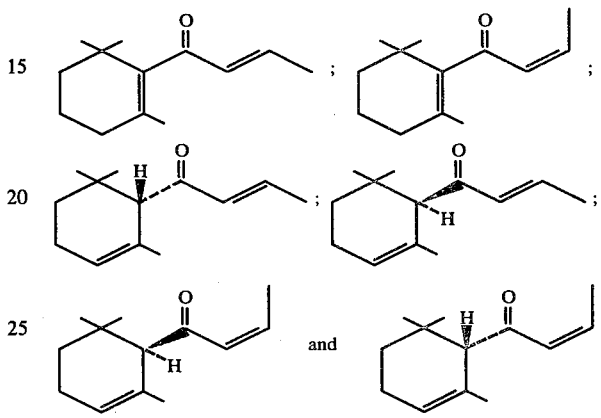

The over-all reaction sequence is as follows:

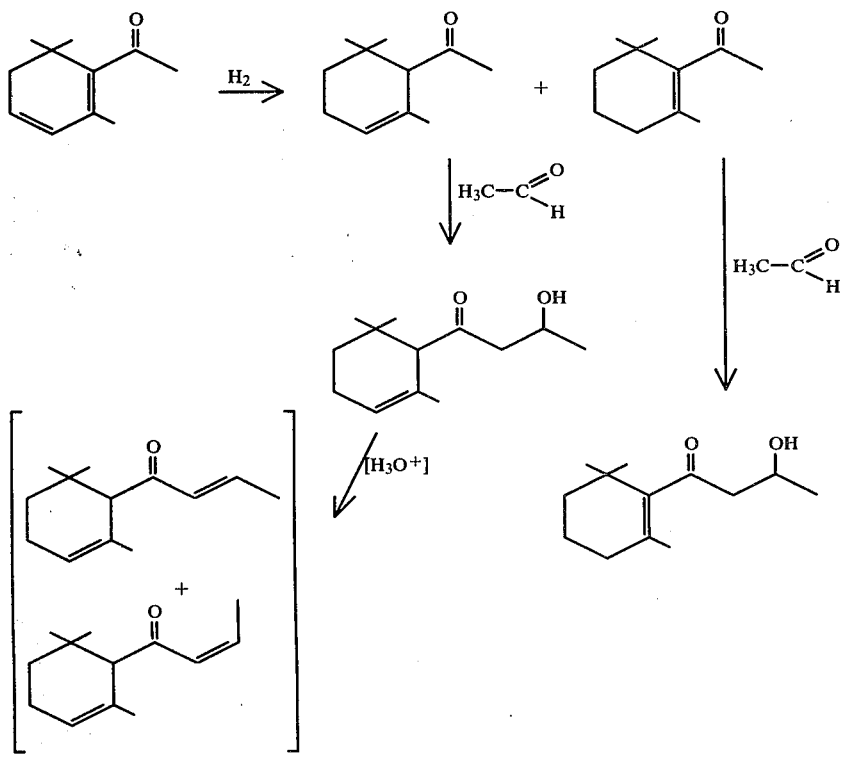

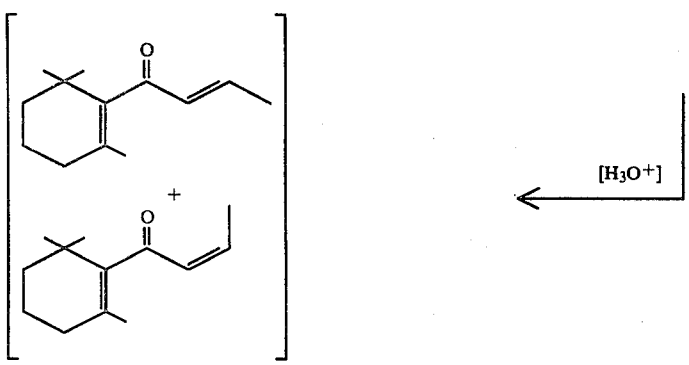

In carrying out the hydrogenation of the 2,6,6-trimethyl-1-acetyl-1,3-cyclohexadiene according to the reaction scheme:

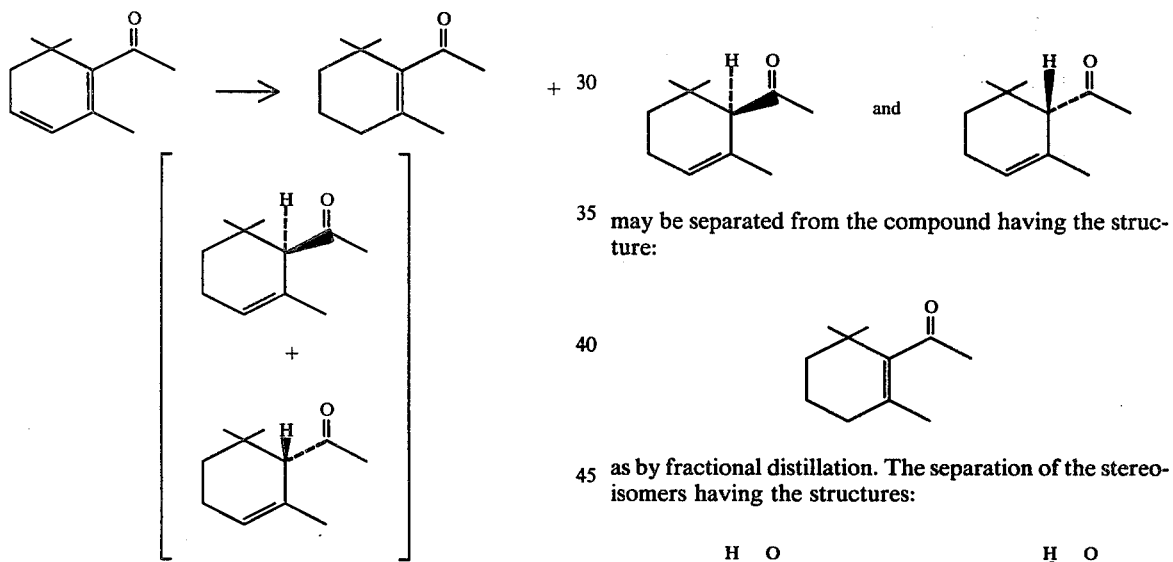

The hydrogenation is carried out at a temperature in the range of from 0° C. up to 100° C. at pressures of from about 1 atmosphere up to about 100 atmospheres using catalysts such as palladium (from 1% up to 10%) on barium sulfate or palladium (from 1% up to 10%) on calcium carbonate in the presence of inert solvents, such as ethyl acetate and catalyst promoters, such as quinoline.

The mole ratio of catalyst:catalyst promoter, e.g., palladium on barium sulfate:quinoline is preferably about 1:1 (weight:weight) but ratios of catalyst:promoter may vary from about 0.25:1 up to about 1:0.25. The weight ratio of 2,6,6-trimethyl-1-acetyl-1,3-cyclohexadiene:inert solvent (e.g., ethyl acetate) may vary from about 1:1 up to about 1:20 with a ratio of about 1:10 (weight:weight) being preferred. At the end of the reaction, the reaction product may, if desired, be separated whereby the compounds having the structures:

may be separated from the compound having the structure:

as by fractional distillation. The separation of the stereoisomers having the structures:

requires a more complicated process, e.g., as by forming "++" or "+−" stereospecific oxime reaction products of the ketones with stereoisomeric amines (e.g., [+] 3-amino-2-methoxy propionic acid ethyl ester having the structure:

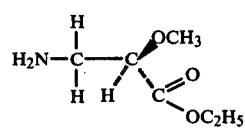

An example of a Shiff base with, for example, (+) 2,6,6-trimethyl-1-acetyl-1,3-cyclohexadiene has the structure:

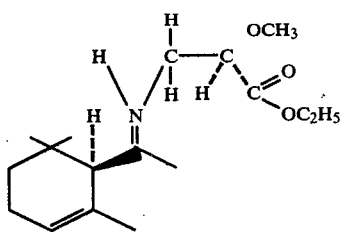

The resulting mixture of stereoisomers can then be separated as by column chromatography on a silica gel column.

The resulting mixture of 2,6,6-trimethyl-1-acetylcyclohexenes is then reacted, if desired, with a lower $C_1$–$C_6$ alkyl Grignard reagent having the structure:

RMgX wherein X is halogen selected from the group consisting of chloro, bromo and iodo whereby a mixture of organometallic compounds is formed having the structures:

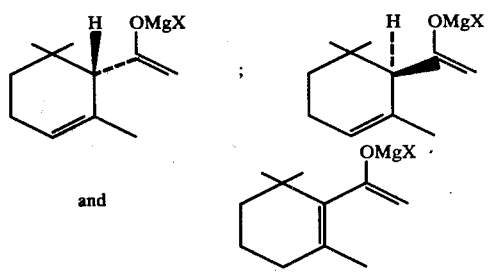

and

On the other hand, one of the Grignard reagents having the structures:

R-MgX may be reacted after separation with one of the compounds having the structures:

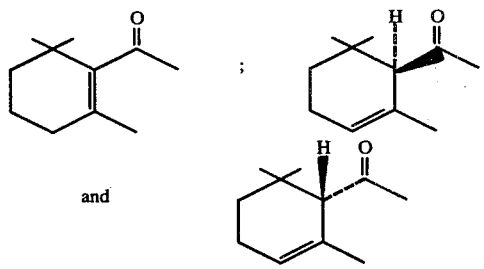

and

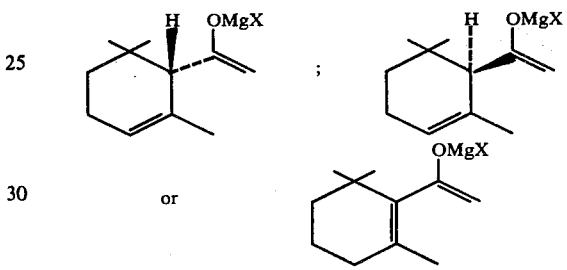

thereby forming a substantially "pure" organometallic compound having one of the structures:

or

The reaction sequence is illustrated according to the following reaction:

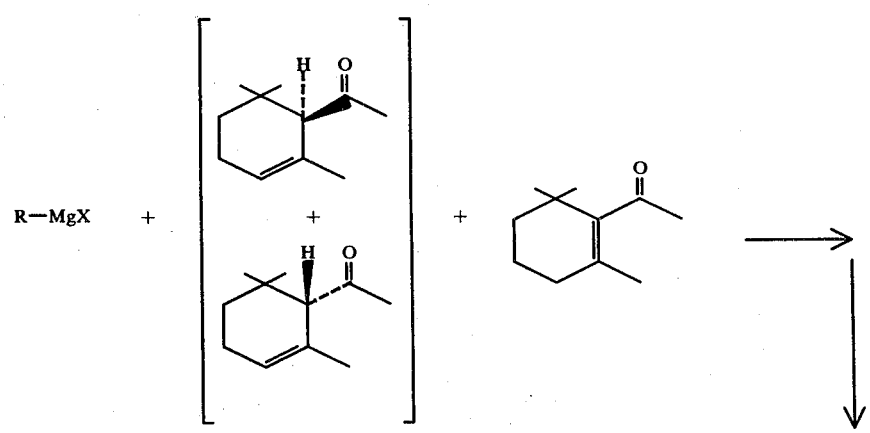

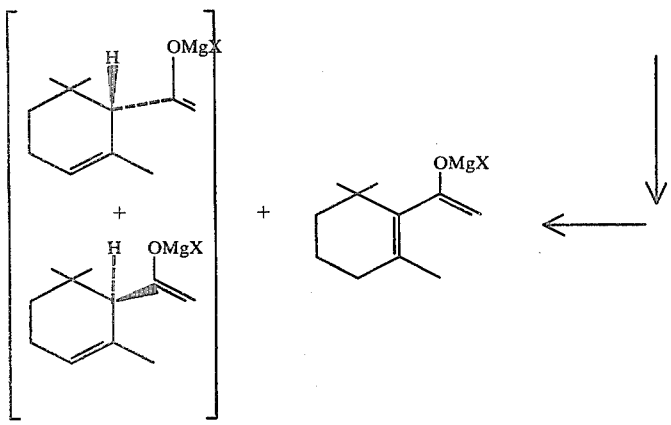

wherein R is $C_1$–$C_6$ lower alkyl and wherein X is halogen selected from the group consisting of chloro, bromo and iodo. This reaction of the lower alkyl Grignard reagent with the 2,6,6-trimethyl-1-acetyl cyclohexene derivative is carried out in the presence of a solvent which is inert in the reaction mass, for example, diethyl ether or tetrahydrofuran. The reaction temperature is preferably between 20° and 35° C. at atmospheric pressure. Higher pressures or lower pressures and higher temperatures and lower temperatures may be used but there is no advantage to so using the temperature outside of 20°–35° C. and pressures outside of one atmosphere (ambient conditions).

After the organometallic compound having the structures:

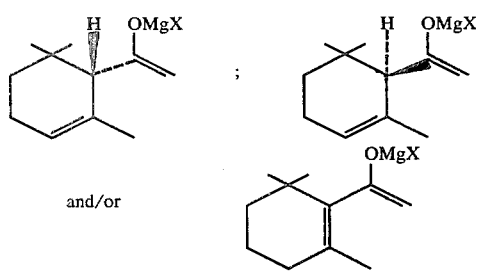

and/or are formed the resulting mixture or individual organometallic compound is reacted with acetaldehyde and then water to form a hydroxy ketone or mixture of hydroxy ketones having one or more of the following structures:

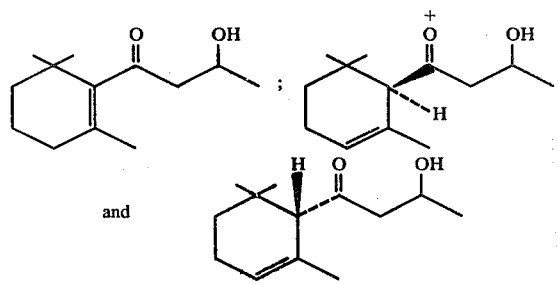

and

The reaction sequence for the reaction of acetaldehyde with one or more of the organometallic compounds having one of the structures:

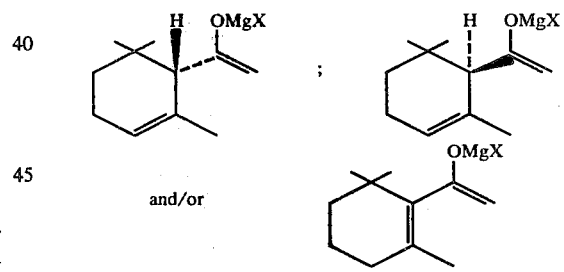

and/or is as follows:

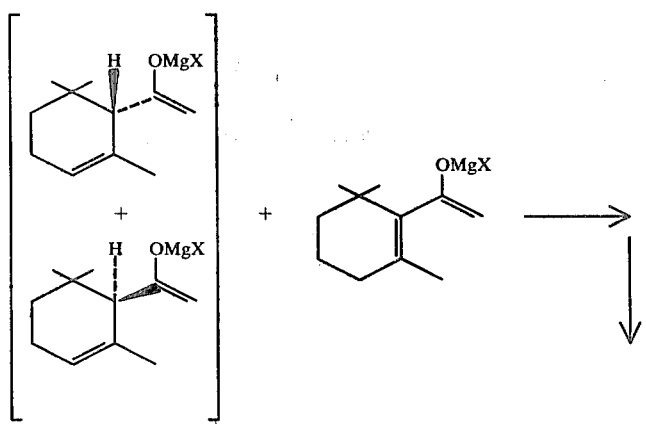

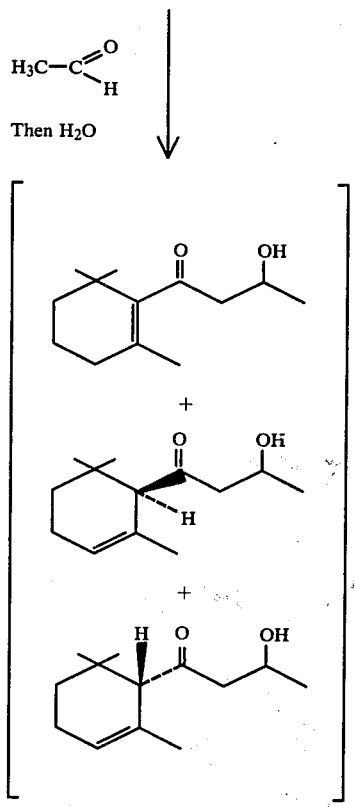

Then H₂O

The reaction temperature for this reaction is preferably between 010° C. and +15° C.; more preferably between 0° C. and 10° C. at atmospheric pressure. The acetaldehyde is added to one or more of the compounds having the structures:

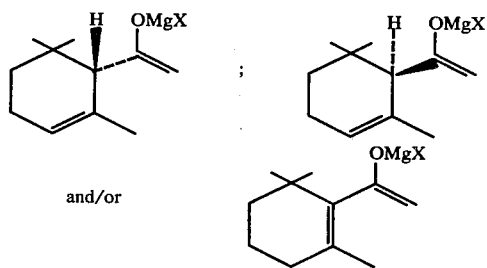

in admixture is an inert solvent such as toluene or xylene. It is preferred that the weight ratio of inert solvent such as toluene or xylene:acetaldehyde be in the range of from about 2:1 up to about 5:1 with a preferred weight ratio of solvent such as toluene or xylene: acetaldehyde being about 3-4:1. After completion of the reaction of one or more of the organometallic compounds having one of the structures:

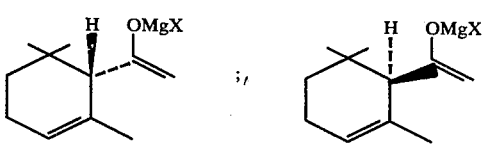

and/or

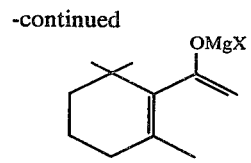

with acetaldehyde, the resulting reaction product is then admixed with water at a temperature of between 10° C. and 40° C., preferably between 15° C. and 25° C. at one atmosphere pressure.

The resulting compound, the hydroxy ketone or mixture of hydroxy ketones having one or more of the structures:

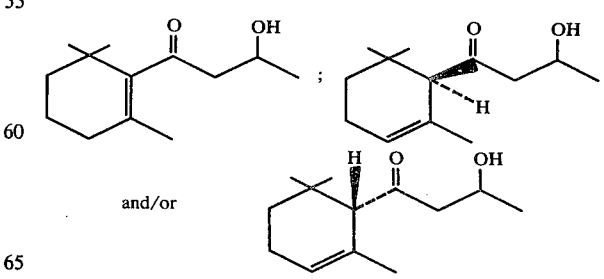

may be separated as by fractional distillation whereby the compounds having the structures:

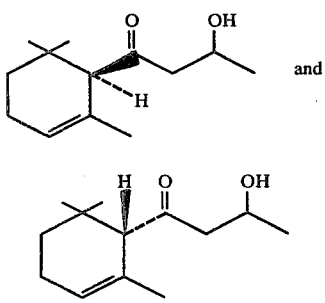 and may be separated from the compound having the structure:

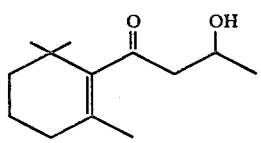

The compounds having the structures:

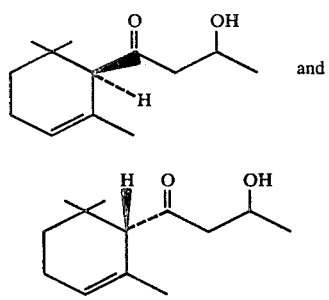 and may also be separated by first forming Shiff bases thereof with such materials as +3-amino-2-methoxy-propionic acid ethyl ester having the structure:

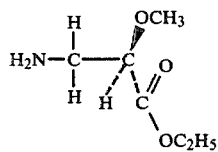

whereby such compounds are formed as have the structure:

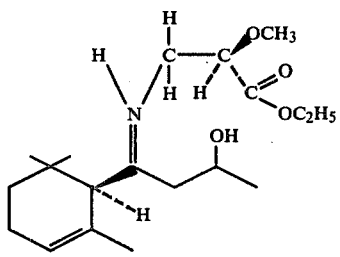

The Shiff bases may then be separated as by column chromatography and the individual stereoisomers may then be hydrolyzed to form the pure stereoisomers.

In the alternative, one or more of the compounds having the structures:

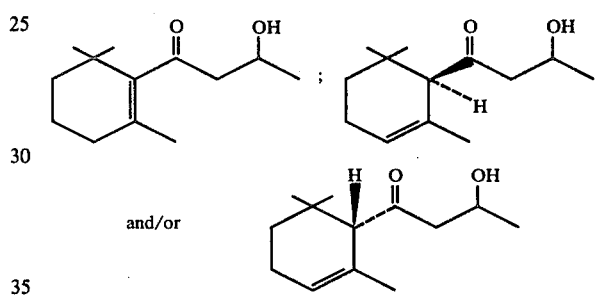

and/or may be dehydrated with a dehydrating agent, such as acetic anhydride whereby α and/or β-damascone isomers may be formed having one or more of the structures:

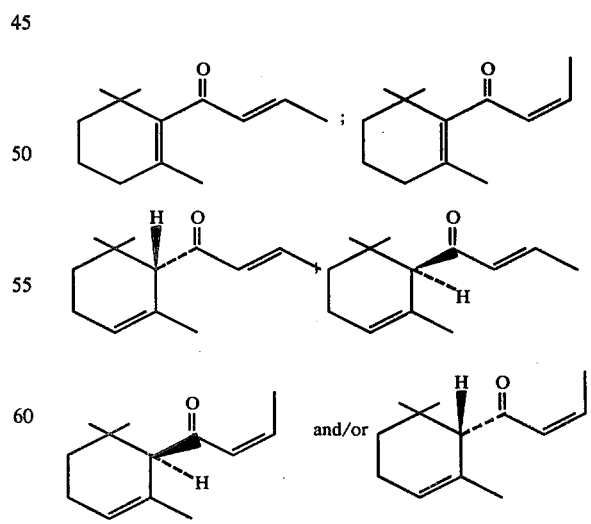

and/or

The reaction sequence for this dehydration reaction is as follows:

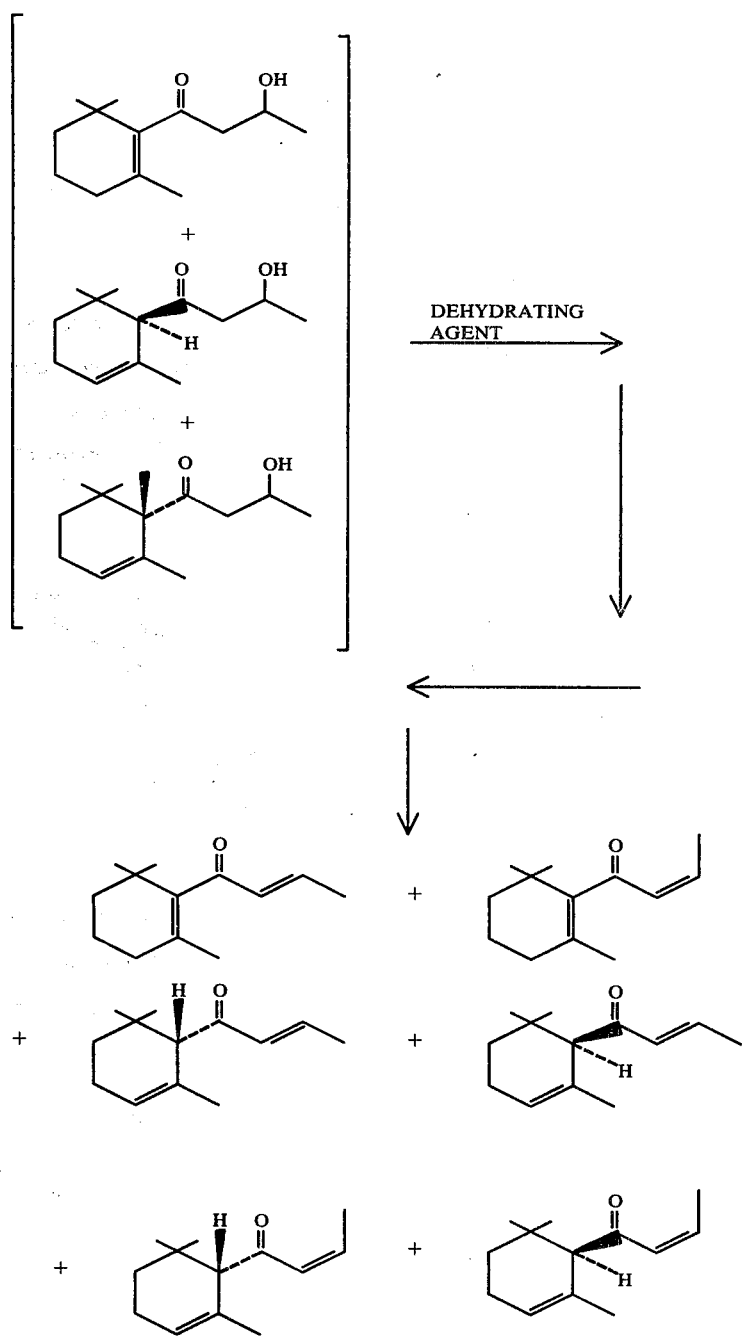

The dehydration reaction takes place in the presence of an inert solvent, such as toluene or xylene and the dehydration reagent is a compound such as acetic anhydride, phosphoric acid or para toluene sulfonic acid. The dehydration also takes place in the presence of a weak base, such as sodium acetate, potassium acetate, sodium carbonate or potassium carbonate. The weight ratio of keto alcohol:solvent may vary from 1:0.5 (keto alcohol): solvent/weight:weight) up to 1:10 with a preferred ratio of between 1:0.5 and 1:1. The mole ratio of keto alcohol:dehydrating agent is preferably between 1:0.25 and 1:1 (keto alcohol:dehydrating agent) and the weight ratio of dehydrating agent:weak base is preferably between 1:1 and 10:1 with a weight ratio of from 4:1 up to 5:1. dehydrating agent:weak base being preferred.

At the point of completion of the reaction, the reaction mass is "worked up" and the isomers, the cis and trans isomers, and the "α" and "β" isomers are separated by fractional distillation. On the other hand, the stereoisomers must be separated only after reaction thereof with stereoisomeric separation reagents, such as (+)3-amino-2-methoxypropionic acid ethyl ester having the structure:

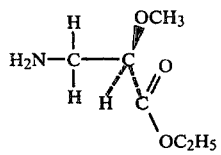

to form such Shiff bases as have the structure:

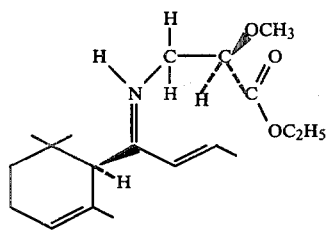

When the 1-acyl-2,6,6-trimethylcyclohexene derivatives according to the process of our invention are used as food flavor adjuvants, the nature of the co-ingredients included with the 1-acyl-2,6,6-trimethylcyclohexene derivatives used in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates the 1-acyl-2,6,6-trimethylcyclohexene derivatives produced according to the process of our invention and in addition sweetening agents which may be sugars, including sucrose or dextrose and/or artifical sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials, lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, $\beta,\beta$-dimethyl acrolein, methyl-n-amyl ketone, n-hexanal, 2-hexenal, isopentanal, hydrocinnanic aldehyde, cis-3-hexenal, 2-heptenal nonyl aldehyde, 4-(p-hydroxyphenyl)-2-butanone, alpha-ionone, beta-ionone, methyl-3-butanone, benzaldehyde, $\beta$-damascone, $\beta$-damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, n-hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alpha-pinene; pyrazines, such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones, such as δ-nonalactone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the acyl-2,6,6-trimethylcyclohexene derivatives of our invention by not covering or spoiling the organoleptic properties (aroma and/or taste) thereof; (ii) be non-reactive with the acyl-2,6,6-trimethylcyclohexene derivatives of our invention and (iii) be capable of providing an environment in which the acyl-2,6,6-trimethylcyclohexene derivatives of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 1-acyl-2,6,6-trimethylcyclohexene derivatives of our invention employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of one or more 1-acyl-2,6,6-trimethylcyclohexene derivatives of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of one or more 1-acyl-2,6,6-trimethylcyclohexene derivatives of our invention ranging from a small but effective amount, e.g., about 0.5 parts per million up to about 100 parts per million based on total food composition or chewing gum composition or medicinal product composition or toothpaste composition are suitable. Concentrations in excess of the maximum quantity stated are not normally recommended since they fail to provide commensurate enhancement of organoleptic properties. In those instances, where one or more 1-acyl-2,6,6-trimethylcyclohexene derivatives of our invention is added to the foodstuff as an integral component of a flavoring composition, it is, of course, essential that the total quantity of flavoring composition employed be sufficient to yield an effective concentration of one or more 1-acyl-2,6,6-trimethylcyclohexene derivatives of our invention in the foodstuff product.

Food flavoring compositions containing one or more of the compounds prepared in accordance with the present invention preferably contain one or more 1-acyl-2,6,6-trimethylcyclohexene derivatives in concentrations ranging from about 0.02% up to about 15% by weight based on the total weight of said flavoring composition.

The composition described herein can be prepared according to conventional techniques well known as typified by cake batters and fruit drinks and can be formulated by merely admixing the involved ingredients within the properties stated in a suitable blender to obtain the desired consistency, homogeneity of dispersion, etc. Alternatively, flavoring compositions in the form of particulate solids can be conveniently prepared by mixing one or more 1-acyl-2,6,6-trimethylcyclohexene derivatives prepared in accordance with our invention with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and one or more 1-acyl-2,6,6-trimethylcyclohexene derivatives of our invention in a dry blender until the requisite degree of uniformity is achieved.

It is presently preferred to combine one or more 1-acyl-2,6,6-trimethylcyclohexene derivatives of our invention with at least one of the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl Acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
β-Damascone (1-crotonyl-2,6,6-trimethylcyclohex-1-ene);
β-Damascenone (1-crotonyl-2,6,6-trimethylcyclohexa-1,3-diene);
Beta-cyclohomocitral (2,6,6-trimethylcyclohex-1-ene carboxaldehyde)
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl) norbornadiene The following examples serve to illustrate our invention but our invention is only intended to be limited as indicated in the appended claims. All parts and percentages given herein are by weight unless otherwise specified.

EXAMPLE I

PREPARATION OF 2,6,6-TRIMETHYLCYCLOHEXA-1,3-DIENE WITH HYDROGEN TO FORM 1-ACETYL-2,6,6-TRIMETHYLCYCLOHEXENE-1 AND -2

Reaction:

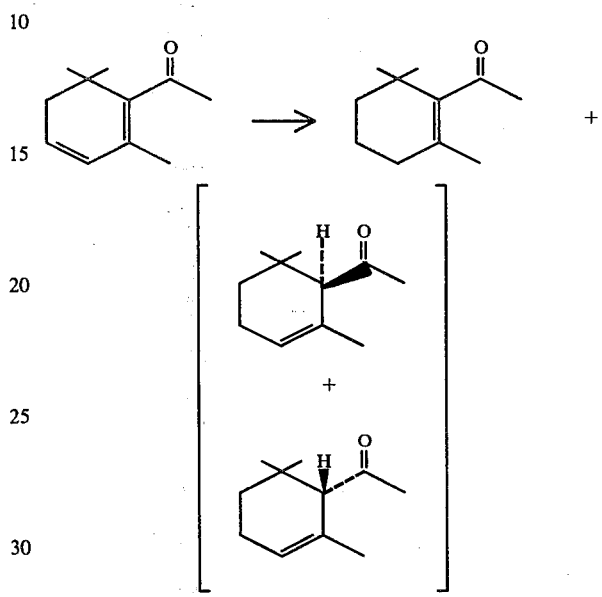

To a 25 ml reaction flask equipped with sample remover system, magnetic stirrer, thermometer and hydrogen addition tube is added 1 gram of 1-acetyl-2,6,6-trimethylcyclohexa-1,3-diene, 10 ml of ethyl acetate and 0.025 grams of quinoline. The resulting mixture is stirred and a reference sample is removed. 0.025 Grams of a catalyst consisting of 5% palladium on barium sulphate is then added and the resulting mixture is hydrogenated to an uptake of 73 ml hydrogen. Hydrogenation is carried out at one atmosphere pressure. NMR, IR and mass spectra analyses yield the information that the resulting material contains compounds having the structures:

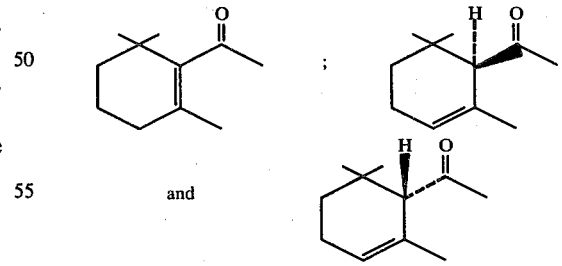

30% of the reaction mass contains compounds having the structures:

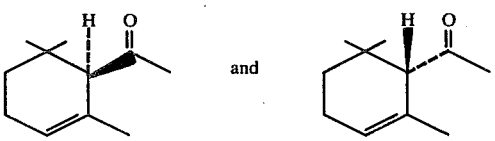

60% of the reaction mass contains a compound having the structure:

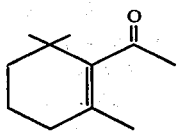

Figure 1:
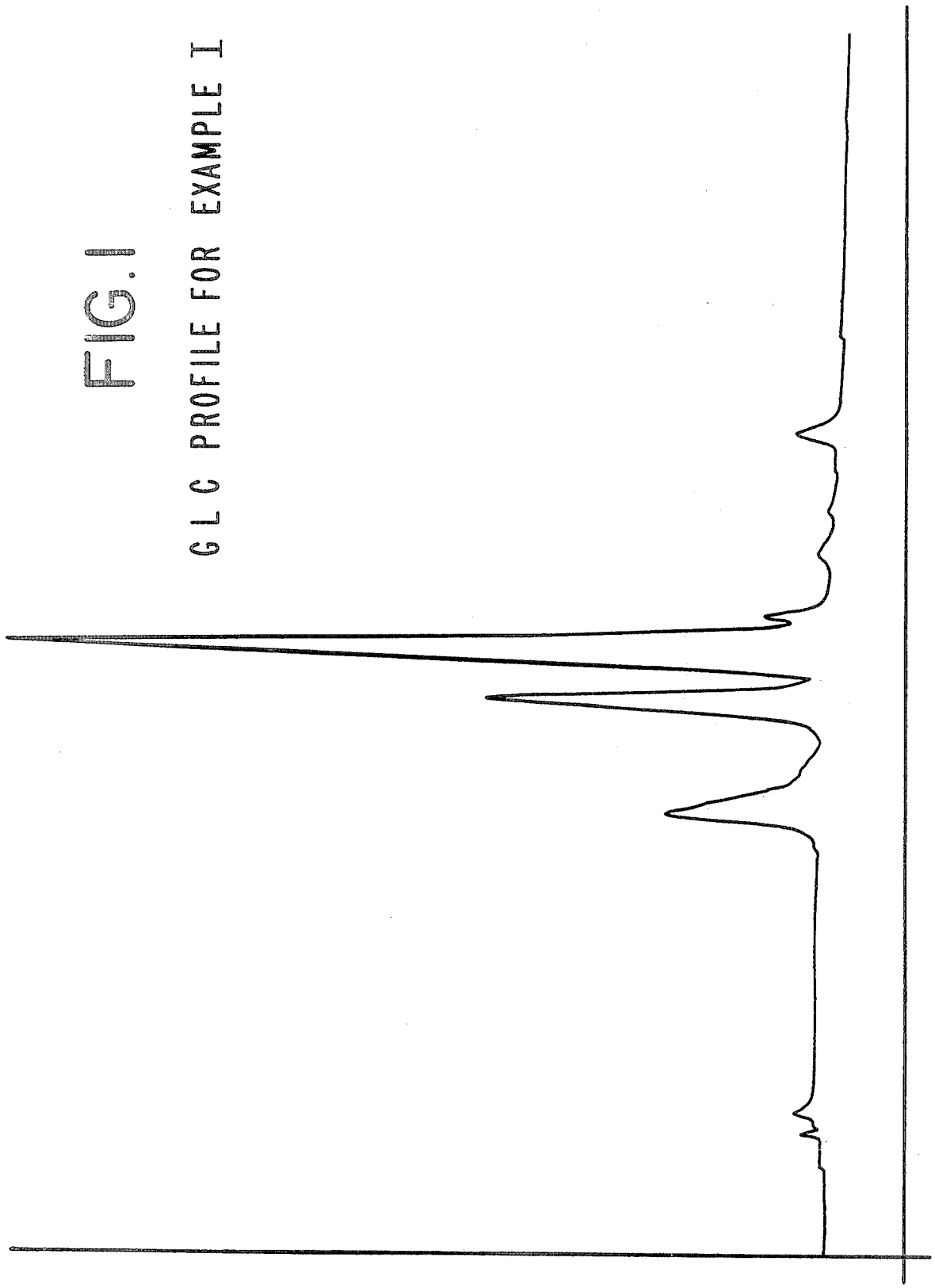
FIG. 1 is the GLC profile for the reaction product of Example I.
Figure 2:
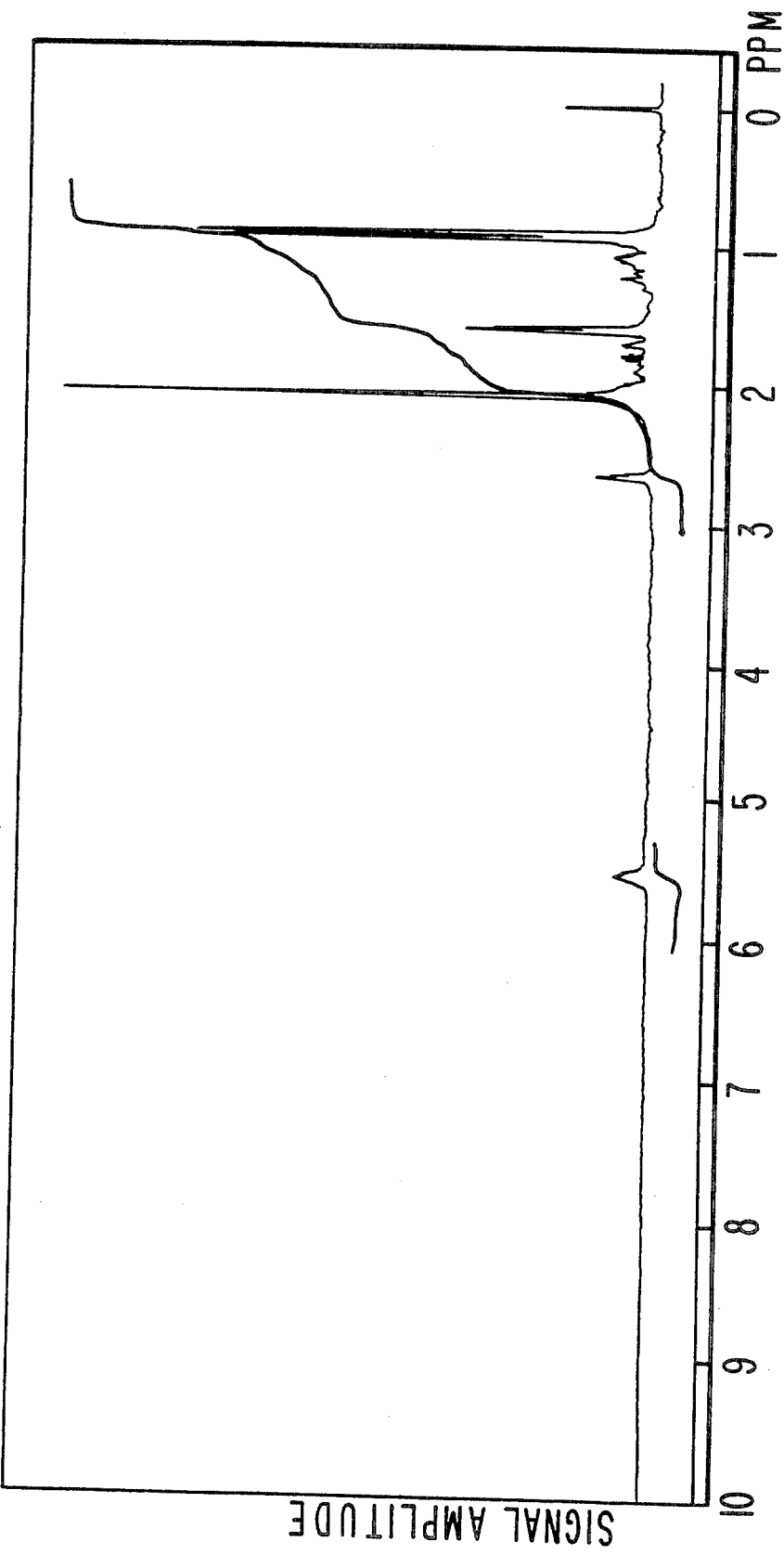
FIG. 2 is the NMR spectrum for peak 2 of Example I, peak 2 consisting essentially of compounds having the structures.

FIG. 1 is the GLC profile for the reaction product immediately after hydrogenation. FIG. 2 is the NMR spectrum for peak 2 of the GLC profile having the structure:

FIG. 3 is the NMR spectrum for peak 3 of the GLC profile consisting essentially of compounds having the structure:

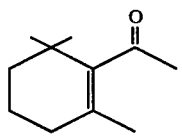

FIG. 4 is the infrared spectrum for peak 2 of the GLC profile having both structures:

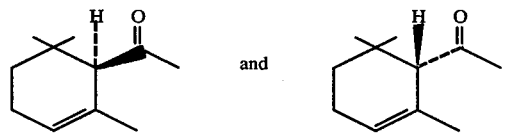

FIG. 5 is the infrared spectrum for peak 2 of the GLC profile consisting of compound having the structure:

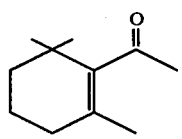

After adding 10 g Primol ® (a hydrocarbon mineral oil manufactured by the Exxon Corporation of Linden, New Jersey), the reaction product is distilled on a micro-Vigreux column yielding the following fractions:

| Fraction No. | Vapor Temp. | Liquid Temp. | Vac. mm. Hg. | Weight of Fraction (grams) |
|---|---|---|---|---|
| 1 | 50/50 | 67/67 | 25/25 | 3.6 |
| 2 | 50 | 67 | 30 | 6.9 |
| 3 | 50 | 67 | 30 | 4.5 |
| 4 | 50 | 67 | 30 | 8.4 |
| 5 | 50 | 67 | 30 | 11.8 |
| 6 | 50 | 75 | 30 | 9.3 |
| 7 | 50 | 90 | 30 | 3.8 |
| 8 | 45 | 190 | 30 | 1.2 |
| | | | | 49.5 |

EXAMPLE II

FLAVOR UTILITY OF 1-ACETYL-2,6,6-TRIMETHYLCYCLOHEXENES

The following lemon flavor formulation is prepared:

| Ingredients | Parts by Weight |
|---|---|
| Natural Lemon Oil, Terpeneless | 10 |
| Acetaldehyde | 0.6 |
| Alpha-terpineol | 2.1 |
| Citral | 1.8 |
| Carvone | 0.24 |
| Terpinolene | 1.2 |
| Alpha-terpinene | 0.25 |
| Diphenyl | 0.25 |
| Alpha Fenchyl Alcohol | 0.25 |
| Limonene | 0.35 |
| Linalool | 0.25 |
| Geranyl Acetate | 0.25 |
| Nootkatone | 0.25 |
| Neryl Acetate | 0.25 |

The flavor formulation is divided into two portions. Four parts per million of the mixture of 1-acetyl-2,6,6-trimethylcyclohexene derivatives produced according to Example I is added to 200 parts per million of the first portion of the lemon flavor prepared above; to the second portion of the lemon flavor nothing is added. A definite aroma improvement, a more natural lemon juice aroma and taste as well as a pleasant sour effect and generally improved taste is created as a result of the addition of the 1-acetyl-2,6,6-trimethylcyclohexene derivative mixture produced according to Example I to the lemon flavor. In general, the 1-acetyl-2,6,6-trimethylcyclohexene derivative mixture supplies a natural "lemon juice" note to this lemon flavor.

EXAMPLE III

The mixture of 1-acetyl-2,6,6-trimethylcyclohexene derivatives prepared according to Example I is added at the rate of 10 ppm to Goya Guava Nectar (manufactured by Goya Manufacturing Co., New York, N.Y.). It is submitted to a bench panel which unanimously considers the guava nectar containing the 1-acetyl-2,6,6-trimethylcyclohexene derivative mixture produced according to Example I to have a fuller natural fresh guava character. The Goya Guava Nectar containing 1-acetyl-2,6,6-trimethylcyclohexene derivative mixture prepared according to Example I is preferred by the bench panel unanimously to the Goya Guava Nectar not containing said mixture of 1-acetyl-2,6,6-trimethylcyclohexene derivatives.

EXAMPLE IV

A. POWDER FLAVOR COMPOSITION

20 Grams of the flavor composition of Example II is emulsified in a solution containing 300 gm gum acacia and 70 gm water. The emulsion is spray-dried with a Bowen Lab Model Drier utilizing 260 c.f.m. of air with an inlet temperature of 500° F., an outlet temperature of 200° F., and a wheel speed of 50,000 rpm.

B. SUSTAINED RELEASE FLAVOR

The following mixture is prepared:

| Ingredients | Parts by Weight |
|---|---|
| Liquid Lemon Flavor Composition of Example II | 20 |
| Propylene glycol | 9 |
| Cab-O-Sil ® M-5 (Brand of Silica produced by the Cabot Corporation of 125 High Street, Boston, Mass. 02110; Physical Properties: Surface area: 200 m²/gm Nominal particle size: 0.012 microns Density: 2.3 lbs/cu.ft) | 5.00 |

The Cab-O-Sil is dispersed in the liquid lemon flavor composition of Example II with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE V

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example II is added to the solution which is then homogenized to form an emulsion having particle size typically in the range of 2-5 microns. This material is kept at 120° F. under which conditions the gelatin will not jell.

Coascervation is induced by adding, slowly and uniformly 40 parts by weight of a 20% aqueous solution of sodium sulphate. During coascervation the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE VI

CHEWING GUM

100 Parts by weight of chicle are mixed with 4 parts by weight of the flavor prepared in accordance with Example IV. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting sour lemon flavor.

EXAMPLE VII

CHEWING GUM

100 Parts by weight of chicle are mixed with 18 parts by weight of the flavor prepared in accordance with Example VI. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting sour lemon flavor.

EXAMPLE VIII

TOOTHPASTE FORMULATION

The following separate groups of ingredients are prepared:

| Parts by Weight | Ingredient |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Luaroyl Sarcosinate (foaming agent) |
| Group "D" | |
| 1.200 | Flavor Material of Example IV |
| 100.00 (Total) | |

PROCEDURE:
1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium n-lauroyl sarcosinate
5. The resultant slurry is then blended for one hour. The completed paste is then transferred to a three roller mill and then homogenized, and finally tubed.

The resulting toothpaste when used in a normal toothbrushing procedure yields a pleasant lemon flavor, of constant strong intensity throughout said procedure (1–1.5 minutes).

EXAMPLE IX

CHEWABLE VITAMIN TABLETS

The flavor material produced according to the process of Example IV is added to a Chewable Vitamin Tablet Formulation at a rate of 10 gm/Kg which chewable vitamin tablet formulation is prepared as follows:

In a Hobart Mixer, the following materials are blended to homogeneity:

| | Gms/1000 Tablets |
|---|---|
| Vitamin C (ascorbic acid) as ascorbic acid-sodium mixture 1:1 | 70.00 |
| Vitamin B₁ (thiamine mononitrate) as Rocoat ® thiamine mononitrate 33-⅓% (Hoffman La Roche) | 4.0 |
| Vitamin B₂ (riboflavin) as Rocoat ® riboflavin 33-⅓% | 5.0 |
| Vitamin B₆ (pyridoxine Hydrochloride) as Rocoat ® pyridoxine hydrochloride 33-⅓% | 4.0 |
| Niacinamide as Rocoat ® niacinamide 33-⅓% | 33.0 |
| Calcium pantothenate | 11.5 |

| | Gms/1000 Tablets |
|---|---|
| Vitamin $B_{12}$ (cyanocobalamin) as Merck 0.1% in gelatin | 3.5 |
| Vitamin E (dl-alpha tocopheryl acetate) as dry Vitamin E acetate 33-⅓% Roche | 6.6 |
| d-Biotin | 0.044 |
| Flavor of Example IV | (as indicated above) |
| Certified lake color | 5.0 |
| Sweetner - sodium saccharin | 1.0 |
| Magnesium stearate lubricant | 10.0 |
| Mannitol g.s. to make | 500.0 |

Preliminary tablets are prepared by slugging with flat-faced punches and grinding the slugs to 14 mesh. 13.5 G dry Vitamin A acetate and 0.6 g Vitamin D are then added as beadlets. The entire blend is then compressed using concave punches at 0.5 g each.

Chewing of the resultant tablets yields a pleasant, long-lasting, consistently strong lemon flavor with a tropical fruit-like background for a period of 12 minutes.

EXAMPLE X

The mixture of 1-acetyl-2,6,6-trimethylcyclohexenes produced according to Example I is added at the rate of 2% to a commercial peppermint oil (Cullison, Wilanette, Redistilled USP). Peppermint oil with and without the 1-acetyl-2,6,6-trimethylcyclohexene produced according to Example I are compared at the rate of 10 ppm in water by a bench panel of experts. The product with the 1-acetyl-2,6,6-trimethylcyclohexene mixture has a more herbaceous, more peppermint, tea, slightly earthy note which is preferred by the bench panel.

What is claimed is:

1. A process for augmenting or enhancing the aroma or taste of a foodstuff having a minty, lemony or tropical fruit aroma or taste comprising the step of adding to said foodstuff from about 0.5 parts per million up to about 100 parts per million based on the foodstuff flavor composition of a mixture consisting essentially of compounds having the structures:

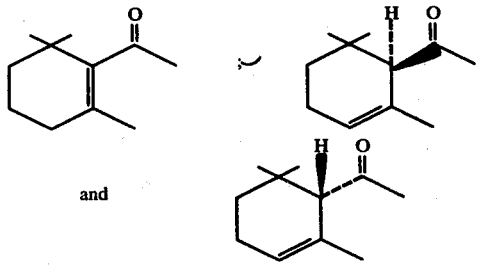

wherein the mixture contains 30% of the compounds having the structures:

and 60% of the compound having the structure:

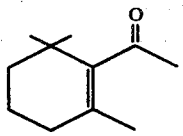

2. A food flavor composition useful for augmenting or enhancing the flavor of a foodstuff having a minty, lemony or tropical fruit aroma or taste comprising (i) from about 0.1% up to about 15% by weight based on the total weight of said flavoring composition of a mixture of 1-acetyl-2,6,6-trimethylcyclohexene derivatives having the structures:

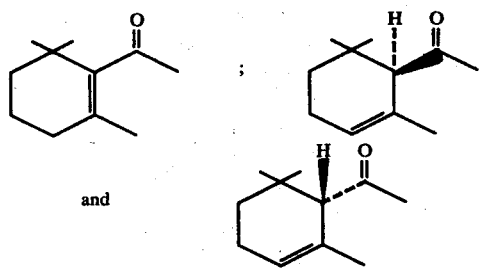

wherein said mixture contains 30% of the compounds having the structures:

and 60% of the compound having the structure:

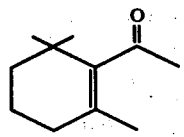

and (ii) the remainder of said composition being at least one adjuvant therefor selected from the group consisting of
p-Hydroxybenzyl acetone;
Geraniol;
Cassis Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl acetate;
Isobutyl acetate;
Cuminaldehyde;

Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
1-Crotonyl-2,2,6-trimethylcyclohex-1-ene;
1-Crotonyl-2,2,6-trimethylcyclohexa-1,3-diene;
2,6,6-Trimethylcyclohex-1-ene carboxaldehyde;
Isoamyl butyrate;
Cis-3-hexenol-1;
2-Methyl-2-pentenoic acid;
4-Allyl-1,2,6-trimethoxybenzene;
4-Propenyl-1,2,6-trimethoxybenzene; and
2-(4-Hydroxy-4-methylpentyl)norbornadiene"

* * * * *